United States Patent
Kato

[11] Patent Number: 6,055,876
[45] Date of Patent: May 2, 2000

[54] NON-CONTACT TYPE INSPECTION SYSTEM

[75] Inventor: Heizaburo Kato, Ogasa-gun, Japan

[73] Assignees: Sankyo Manufacturing Co., Ltd.; Eisai Co., Ltd., both of Japan

[21] Appl. No.: 08/981,154

[22] PCT Filed: May 1, 1997

[86] PCT No.: PCT/JP97/01499

§ 371 Date: Dec. 12, 1997

§ 102(e) Date: Dec. 12, 1997

[87] PCT Pub. No.: WO97/42480

PCT Pub. Date: Nov. 13, 1997

[51] Int. Cl.[7] .................................................. G01D 21/00
[52] U.S. Cl. ..................................... 73/866.5; 250/223 B
[58] Field of Search ............................... 73/865.8, 866, 73/866.5, 800, 863.43, 863.45, 863.53, 863.54, 863.56, 863.57, 864.85; 356/240, 428; 250/223 B

[56] References Cited

U.S. PATENT DOCUMENTS

| | | | |
|---|---|---|---|
| 4,172,524 | 10/1979 | Holm et al. | 250/223 B |
| 4,852,415 | 8/1989 | Bogatzki et al. | 73/865.8 |
| 5,168,224 | 12/1992 | Maruizumi et al. | 324/300 |
| 5,392,644 | 2/1995 | Frazier | 73/162 |

*Primary Examiner*—Hezron Williams
*Assistant Examiner*—Chad Soliz
*Attorney, Agent, or Firm*—Morrison & Foerster LLP

[57] ABSTRACT

The present invention relates to a non-contact type inspection system for inspection of test samples being conveyed, using a non-contact type inspection device, to judge the quality of the test samples automatically. The non-contact type inspection system comprises an annular rotary table which is rotated to convey test samples, an inspection device mounting table disposed inside and outside the rotary table, and having a CCD camera and the like as a non-contact type inspection device for inspection of the test samples being mounted on the inspection device mounting table, a rotary head which is supported above the rotary table and rotatably about the rotation center of the rotary table to hold the upper portions of the test samples being conveyed by the rotary table, and an interlocking mechanism for rotating the rotary head in synchronism with the rotary table. With this construction, the inspection ability of the non-contact type inspection device can be exhibited to a satisfactory extent, the layout of the inspection device can be designed freely, and the inspection of test samples by the inspection device can be performed with a high accuracy and over a wide range.

17 Claims, 11 Drawing Sheets

NON-CONTACT TYPE INSPECTION SYSTEM

FIELD OF THE INVENTION

The present invention relates to a non-contact type inspection system in which test samples being conveyed are each inspected by means of a non-contact type inspection device to judge the quality thereof automatically.

BACKGROUND OF THE INVENTION

According to conventional inspection systems of this type, various products such as, for example, chemicals or electronic components, are inspected as test samples with a high accuracy by means of various non-contact type inspection devices which utilize, for example, the transmissivity or reflectivity of light, to prevent distribution of products of poor quality to commodity distribution channels (see Japanese Examined Patent Publication No. Showa 47-10466, Japanese Unexamined Patent Publication (Kokai) No. Showa 50-11094, Japanese Examined Patent Publication No. Showa 57-11416, Japanese Unexamined Patent Publication (Kokai) No. Showa 57-142252, Japanese Examined Patent Publication No. Showa 60-20695, Japanese Unexamined Patent Publication (Kokai) No. Showa 60-98341, Japanese Unexamined Patent Publication (Kokai) No. Showa 61-282219, Japanese Examined Patent Publication No. Showa 62-15821, Japanese Unexamined Patent Publication (Kokai) No. Showa 64-31040 and Japanese Unexamined Patent Publication (Kokai) No. Heisei 3-96841).

According to a conventional non-contact type inspection system, test samples are conveyed so as to pass a photographing area of an inspection device, e.g. CCD camera, then is each photographed by the CCD camera and the image thus obtained is processed by an image processor to check the quality of the test sample.

In such a conventional non-contact type inspection system, if the test samples are transparent containers made of glass or a plastic material such as, for example, ampoules or vials which contain chemicals, food or drink, light is passed through each of the containers, using an optical inspection device, and is photographed by the CCD camera, whereby even whether a foreign matter is mixed in the inside liquid of each container can be judged precisely.

FIGS. 10 and 11 illustrate a principal portion of a conventional non-contact type inspection system 2 wherein test samples are ampoules 1. The ampoules 1 are conveyed while being put on seats 3a formed on a rotary table 3. A table 8 is disposed inside the rotary table 3 which conveys the ampoules 1, while a table 8a is disposed outside the rotary table 3. Light is emitted from an electric light 4 disposed on the inner table 8 and is passed through each ampoule 1 from the back side of the ampoule 1, then is photographed by a CCD camera 5 disposed on the outer table 8a.

The inspection system 2 is provided with caps 6 whereby the ampoules 1 being conveyed with rotation of the rotary table 3 are pressed from above and are thereby held stably. The caps 6 are attached a large number to the upper portion of a cylindrical drum 7 in the circumferential direction of the drum 7. The drum 7, which is mounted on the rotary table 3 integrally, is rotated together with the rotary table 3 so that the caps 6 can move rotatively together with the ampoules 1 which are moved rotatively. The caps 6 can move vertically through sliding rods 6a to receive and subsequently hold the ampoules 1.

In the conventional non-contact type inspection system 2, the drum 7, which is mounted on the rotary table 3 for co-rotation with the same table 3, has a cylindrical wall 7a, and this cylindrical wall 7a, located behind the ampoules 1, shields the ampoules 1 from the electric light 4. Therefore, for causing the light from the electric light 4 to pass through the ampoules 1 in the inspection work, slits 9 are formed in the cylindrical wall 7a in positions corresponding to the positions of the caps 6, allowing the light from the electric light 4 to be radiated to the backs of the ampoules 1.

However, the quantity of light radiated through the slits 9 formed in the cylindrical wall 7a is limited, and the slits 9 limits the irradiation angle. Consequently, the layout of the CCD camera 5 to be disposed in corresponding relation to the electric light 4 is also limited. Thus, there has been the problem that the inspection cannot be done with a high accuracy and over a wide range.

SUMMARY OF THE INVENTION

The present invention has been accomplished in view of the above-mentioned problem of the prior art and provides a non-contact type inspection system capable of allowing non-contact type inspection devices to exhibit their inspection ability to a satisfactory extent, permitting a more free layout of the inspection devices, and capable of inspecting test samples with a high accuracy and over a wide range, using the inspection devices.

In order to achieve the above-mentioned object, the non-contact type inspection system of the present invention comprises an annular rotary table which is rotated to convey test samples, an inspection device mounting table disposed inside and outside the rotary table in a sandwiching relation to the rotary table, and having a non-contact type inspection device for inspection of the test samples being mounted on the inspection device mounting table, a rotary head which is supported above the rotary table and rotatably about the rotation center of the rotary table to hold the upper portions of the test samples being conveyed by the rotary table, and an interlocking mechanism for rotating the rotary head in synchronism with the rotary table.

Preferably, the rotary head is supported vertically movably.

Preferably, the interlocking mechanism includes a planetary gear mechanism which comprises a pair of first and second internal gears formed in the rotary table and the rotary head, respectively, a pair of first and second planetary gears meshing with the first and second internal gears, respectively, and a connecting shaft supported by the inspection device mounting table to connect the first and second planetary gears integrally with each other.

Preferably, the first and second internal gears have the same module and are integrally formed on the inner periphery of the rotary table and the inner periphery of the rotary head, respectively, the first and second planetary gears also have the same module, and the connecting shaft for connection of both planetary gears is supported rotatably by a bearing member provided on the inspection device mounting table.

Preferably, the rotary head is supported vertically movably and the second planetary gear meshing with the second internal gear in the rotary head is formed axially long in proportion to the vertical displacement of the rotary head.

Preferably, the non-contact type inspection system further includes a holding frame disposed above the rotary table and formed with a vertically extending slide groove, an annular lift frame mounted to the holding frame vertically movably through the slide groove, and a bearing provided on the inner periphery of the lift frame to support the outer periphery of the rotary head rotatably, wherein the rotary head being suspended from the holding frame vertically movably and rotatably through the lift frame.

Preferably, the non-contact type inspection system further includes the lift frame which is mounted to the holding frame vertically movably through the slide groove, bolts supported rotatably by the holding frame and screwed to be engaged with the lift frame, and a power transfer mechanism comprising sprockets mounted on the bolts and a chain entrained on the sprockets for the transfer of a driving force.

Preferably, the inspection device mounting table is provided rotatably around the rotation center of the rotary table, and the non-contact type inspection system further includes a rotation input shaft which is driven rotatively, and having a continuous rotation drive cam and a pivotal rotation drive cam being coaxially mounted on the rotation input shaft side by side, a continuous rotation output shaft which is rotated continuously through a turret, the turret being in sliding contact with the continuous rotation drive cam, and a pivotal rotation output shaft which is rotated pivotally through a turret, the turret being in sliding contact with the pivotal rotation drive cam. The rotary table is rotated continuously by the continuous rotation output shaft, the inspection device mounting table is pivotally rotated by the pivotal rotation output shaft, and when the inspection device mounting table is rotated in the same direction as the rotating direction of the rotary table, the inspection device mounting table is rotated in synchronism with the rotary table.

Preferably, the rotary table is provided with an input gear, an output gear is provided on the continuous rotation output shaft and is in mesh with the input gear, the turret associated with the continuous rotation output shaft is circular and is mounted on the continuous rotation output shaft, and cam followers are provided rotatably on the outer periphery of the circular turret so as to come into sliding contact with the continuous rotation drive cam.

Preferably, a support shaft is provided at a rotation center position of the inspection device mounting table, the pivotal rotation output shaft is connected to the support shaft, the turret associated with the pivotal rotation output shaft is sectorial and is mounted on the pivotal rotation output shaft, and cam followers are provided rotatably on the outer periphery of the sectorial turret so as to come into sliding contact with the pivotal rotation drive cam.

Preferably, the continuous rotation drive cam and the pivotal rotation drive cam, which determine the rotating speed of the rotary table and that of the inspection device mounting table, have cam curves designed such that at a timing at which the inspection device mounting table rotates in the same direction as the rotating direction of the rotary table, the rotating speed of the inspection device mounting table and that of the rotary table are equal to each other, while at a timing at which the inspection device mounting table rotates in the direction opposite to the rotating direction of the rotary table, the rotating speed of the inspection device mounting table is higher than that of the rotary table.

Preferably, the rotary table is formed in an annular shape, the inspection device mounting table comprises an inner table disposed in a space inside the rotary table and an outer table disposed in a space outside the rotary table in an opposed relation to the inner table, a support shaft is integrally provided at a rotation center position of the inner table, an arm extending to the outside of the rotary table is integrally provided on the support shaft, and the outer table is integrally mounted to the arm.

Preferably, the non-contact type inspection device is disposed on each of the inner table and the outer table in an opposed relation with the rotary table and the test samples being conveyed are located therebetween.

Preferably, the non-contact type inspection device comprises a projector for radiating light to be reflected by each of the test samples and a CCD camera for photographing each of the test samples to obtain an image thereof, the projector and the CCD camera being disposed on the inner table and the outer table, respectively, an image of the reflection reflected by the test sample by the light radiated from the projector is photographed by the CCD camera and the test sample is inspected on the basis of the image thereof thus obtained.

Preferably, the non-contact type inspection device comprises a backlight for radiating light to pass through each of the test samples and a transmission type sensor for sensing the thus-transmitted light, the backlight and the transmission type sensor being disposed on the inner table and the outer table, respectively, and the transmitted light through each test sample after radiation from the backlight is sensed by the transmission type-sensor to inspect the test sample.

Preferably, the non-contact type inspection device utilizes X-rays and/or an electromagnetic wave.

Preferably, the rotary head is provided with stems inserted therein vertically slidably and springs for urging the stems downward, and caps for holding the upper portions of the test samples are provided respectively at the lower ends of the stems.

Preferably, a feed line for feeding the test samples onto the rotary table and a discharge line for discharging the test samples from the rotary table are disposed around the rotary table spaced apart from each other in the circumferential direction of the rotary table.

In the non-contact type inspection system of the present invention constructed as above, the rotary head is supported above the rotary table so as to be rotatable about the rotation center of the rotary table. The rotary head is rotated in synchronism with the rotary table by means of the interlocking mechanism. Consequently, when test samples are conveyed by the rotary table, their upper portions are held by the rotary head rotating in synchronism with the rotary table. When test samples being conveyed by both of the rotary table and the rotary head pass through the inspection device mounting table portions disposed respectively inside and outside the annular rotary table, they are each inspected by non-contact type inspection devices mounted on the said table portions.

In particular, since the rotary head which holds the upper portions of test samples is supported above the rotary table, an open space not shielded at all is formed throughout the whole circumferences of both rotary table and rotary head above the rotary table and below the rotary head. Thus, when inspection is made, using non-contact type inspection devices, for the test samples which are conveyed on the rotary table while being held their upper portions by the rotary head, there is nothing that obstructs the inspection between the inspection devices and the test samples. Consequently, the inspection ability of the inspection devices for the test samples can be exhibited to a satisfactory extent without any loss. Besides, it becomes possible to freely arrange the inspection devices for test samples and hence the inspection of the test samples by the inspection devices can be done with a high accuracy and over a wide range.

Moreover, the space above the rotary table, which is also the space above the test samples, is a dead space including no obstacle in the system structure, and the rotary head is supported in this dead space.

Further, if the rotary head is supported vertically movably, the test sample holding position by the rotary head varies up and down, that is, it becomes possible to inspect plural test samples of different heights using a single inspection system.

Additionally, the interlocking mechanism comprises a pair of first and second internal gears provided on the rotary table and the rotary head, respectively, a pair of first and second planetary gears meshing with the first and second internal gears, respectively, and a connecting shaft supported rotatably by the inspection device mounting table to connect the first and second planetary gears integrally with each other. When the first internal gear is rotated together with the rotary table, the first planetary gear meshing with the first internal gear and the second planetary gear connected with the first planetary gear are rotated, and the second internal gear meshing with the second planetary gear is also rotated, whereby the rotary head is rotated in synchronism with the rotary table.

In particular, since the first and second planetary gears are supported by the inspection device mounting table, even if the inspection device mounting table is a fixed type or even if it is a rotary type table which is relatively rotated as necessary with respect to the rotary table, it is possible to let the first and second internal gears rotate at an equal speed, so that the rotary table and the rotary head are rotated always synchronously.

Further, in the non-contact type inspection system according to the present invention, when the rotation input shaft is rotated to rotate both continuous rotation drive cam and pivotal rotation drive cam, the rotary table is rotated continuously by the former continuous rotation drive cam via the turret and the continuous rotation output shaft and the inspection device mounting table is pivotally rotated to and fro in a same direction as and opposite to the rotating direction of the rotary table via the turret and the pivotal rotation outer shaft. The rotary table which rotates continuously conveys the test samples continuously. On the other hand, the inspection device mounting table, when it is rotated in the same direction as the rotating direction of the rotary table, is rotated in synchronism with the rotary table. Accordingly, the non-contact type inspection device mounted on the inspection device mounting table is moved together and synchronously with the test samples being conveyed by the rotary table. This synchronous rotation of both tables permits the non-contact type inspection device to inspect the test samples, whereby there can be created a state as if still test samples are inspected by a still inspection device.

As described above, even during inspection of the test samples, the test samples can be conveyed continuously by the rotary table. After the non-contact type inspection device is rotated on the inspection device mounting table in the same direction as the rotating direction of the rotary table and is moved together with the test samples and the inspection of the test samples is over, the inspection device mounting table is rotated in the direction opposite to the rotating direction of the rotary table to return its original position, for the next inspection work.

In particular, the continuous rotation of the rotary table and the pivotal rotation of the inspection device mounting table can be obtained by the use of the continuous rotation drive cam and the pivotal rotation drive cam, respectively. The application of cams above described, since there is no backlash in a series of motion transfer, always realizes the accurate operation and enhances the accuracy of rotational motion of the tables.

DETAILED DESCRIPTION OF THE INVENTION

An embodiment of the present invention will be described in detail hereinafter with reference to the accompanying drawings. FIGS. 1 to 9 illustrate one embodiment of a non-contact type inspection system according to the present invention.

A non-contact type inspection system 10 embodying the present invention comprises an annular rotary table 12 which has a circular opening formed inside and which is driven rotatively, an inner table 14a disposed inside the rotary table 12 so as to be rotatable about the rotation center of the rotary table 12, and an outer table 14b disposed outside the rotary table 12 so as to be rotatable about the rotation center of the rotary table 12. An inspection device mounting table 14 is constituted by the inner table 14a and the outer table 14b.

Figure 2:
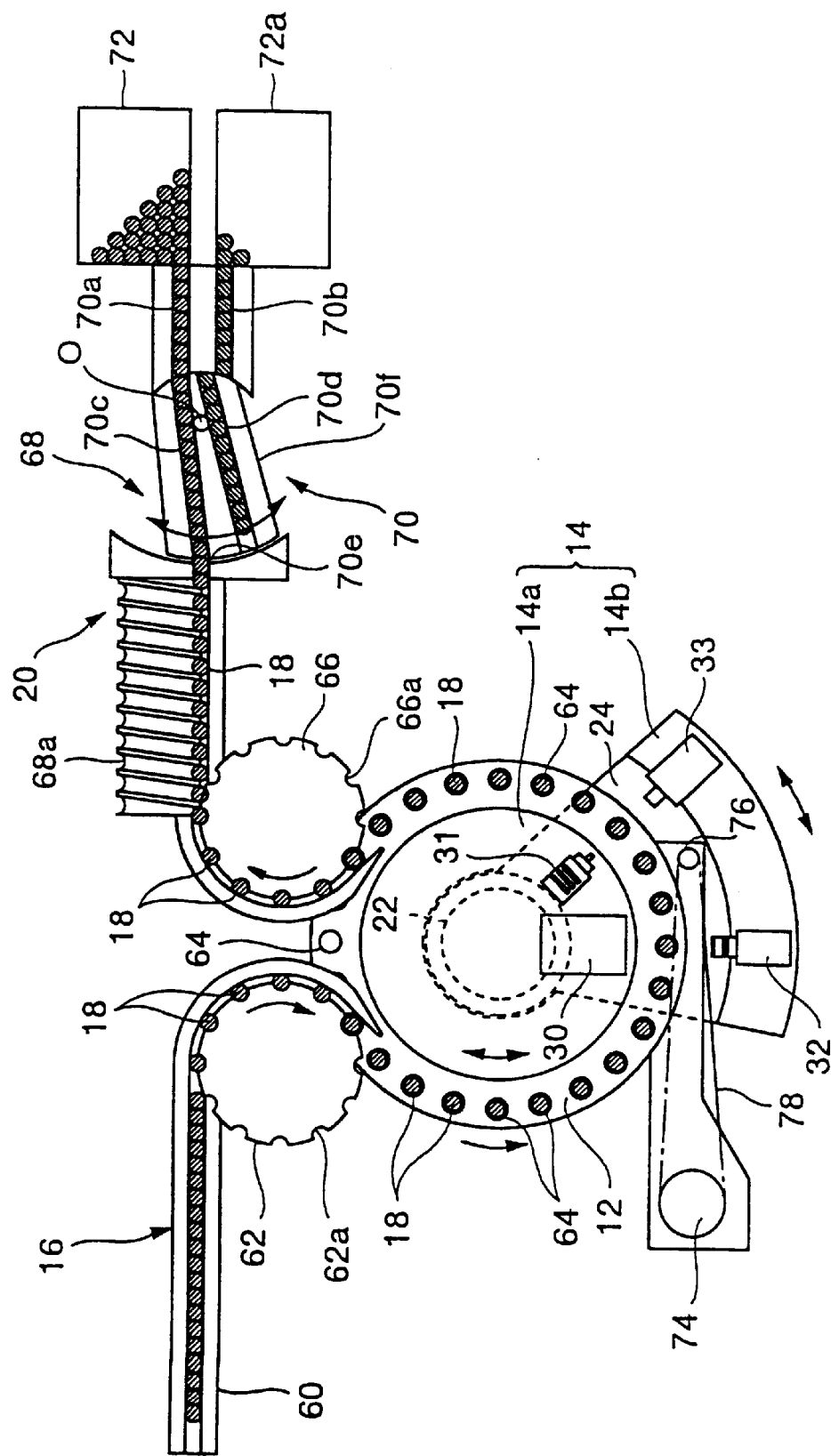
FIG. 2 is a plan view explaining the flow of products to be inspected as test samples in the inspection system.

As shown in FIG. 2, the rotary table 12 is adapted to place products 18 to be inspected as test samples thereon and convey them. The products 18 are received onto the rotary table 12 from a feed line 16, the rotary table 12 rotates with the products 18 carried thereon, and the products 18 after inspected are discharged through a discharge line 20.

Figure 1:
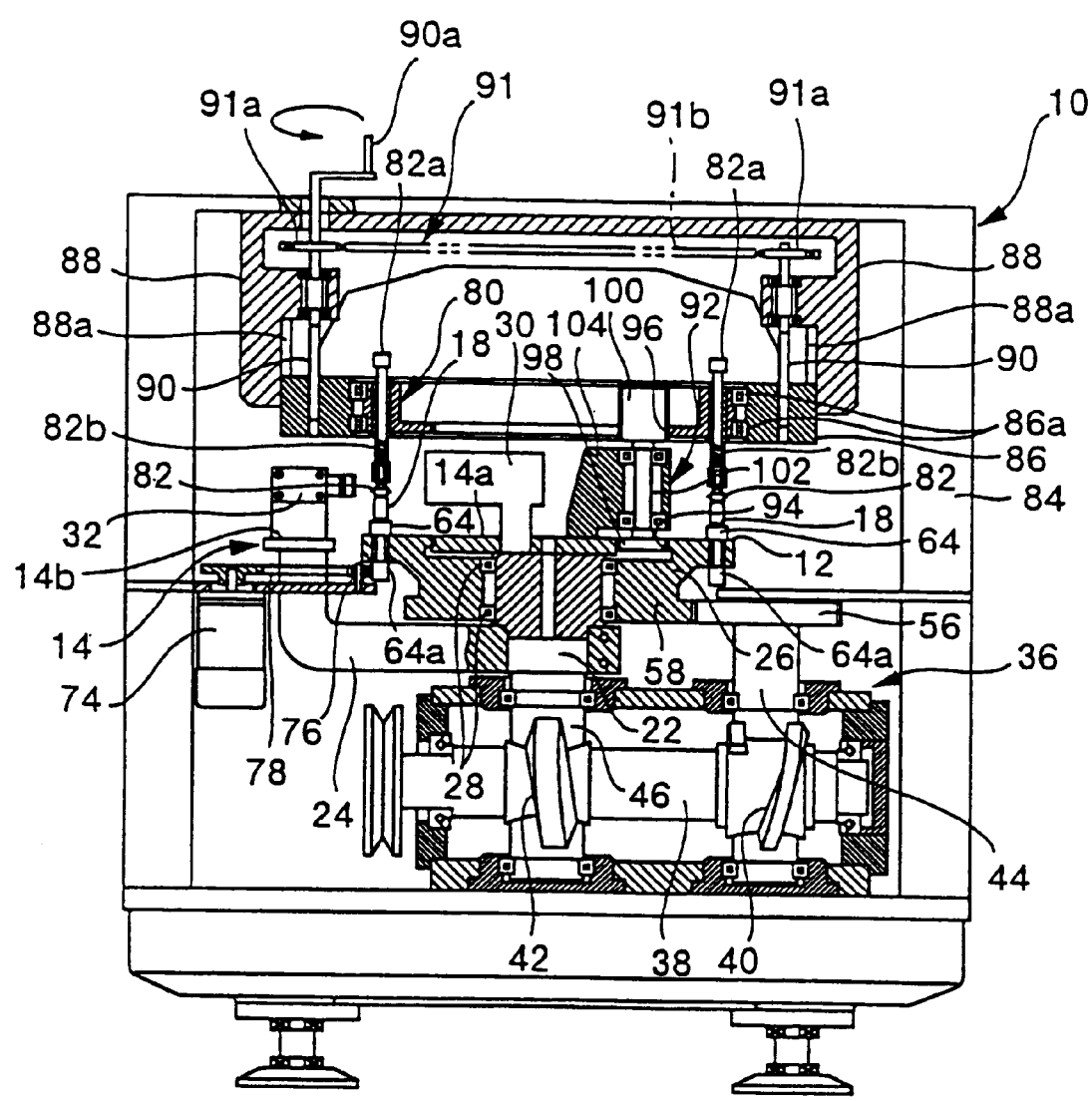
FIG. 1 is a sectional front view showing the whole of a non-contact type inspection system according to an embodiment of the present invention.
Figure 3:
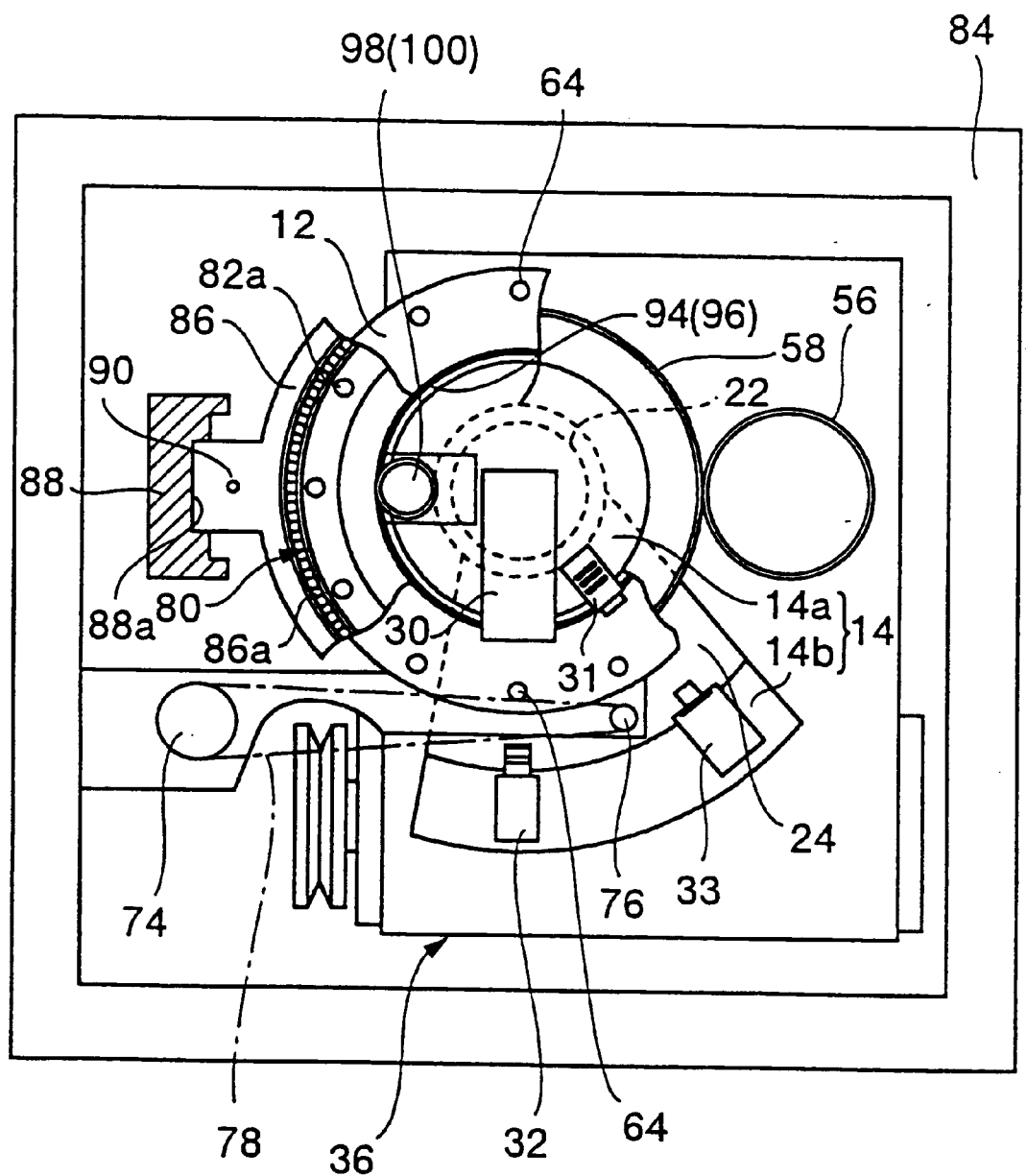
FIG. 3 is a sectional plan view showing a principal portion of the inspection system.

The inner table 14a is formed in the shape of a disk, and a support shaft 22 is integrally attached at the under side of the central part of the inner table 14a, as shown in FIGS. 1 and 2. On the other hand, the outer table 14b, as shown in FIGS. 2 and 3, is formed in the shape of an arcuate belt exceeding about one sixth of the circumference of the rotary table 12, and a sectorial arm 24 is integrally projected from the underside of the outer table 14b. A pivot portion of the sectorial arm 24 is integrally fitted on the lower portion of the support shaft 22 of the inner table 14a, whereby the inner and outer tables 14a and 14b are rendered integral with each other. Further, a boss portion 26 is integrally formed on the lower surface of the rotary table 12 and it is fitted on the upper portion of the support shaft 22 rotatably through bearings 28.

As shown in FIG. 2, a projector 30 and a transmission type sensor 31 are mounted on the inner table 14a, while a CCD camera 32 and a backlight 33 are mounted on the outer table 14b. The projector 30 and the CCD camera 32, as well as the transmission type sensor 31 and the backlight 33, as non-contact type inspection devices to inspect the products 18 to be inspected, are disposed opposedly to each other in a sandwiching relation to the products 18 which are conveyed by the rotary table 12.

Below the rotary table 12 and the inspection device mounting table 14 is disposed a cam mechanism 36 for driving both tables 12 and 14. The cam mechanism 36 is provided with a rotation input shaft 38 to which is inputted a rotating force from a rotative drive source (not shown). A continuous rotation drive cam 40 and a pivotal rotation drive cam 42 are coaxially mounted on the rotation input shaft 38 spaced apart each other.

Figure 4:
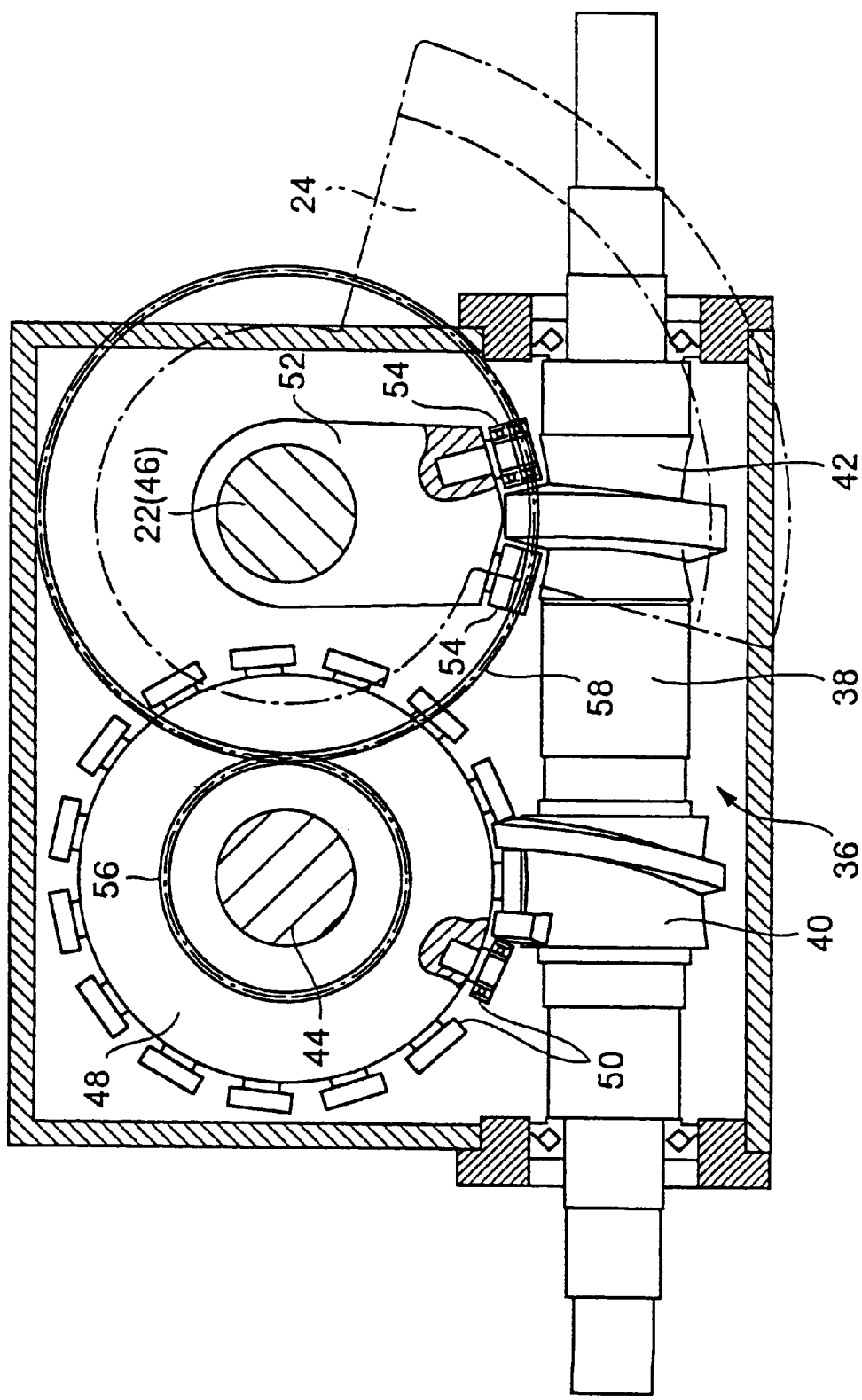
FIG. 4 is a plan view showing a cam mechanism used in the inspection system.
Figure 5:
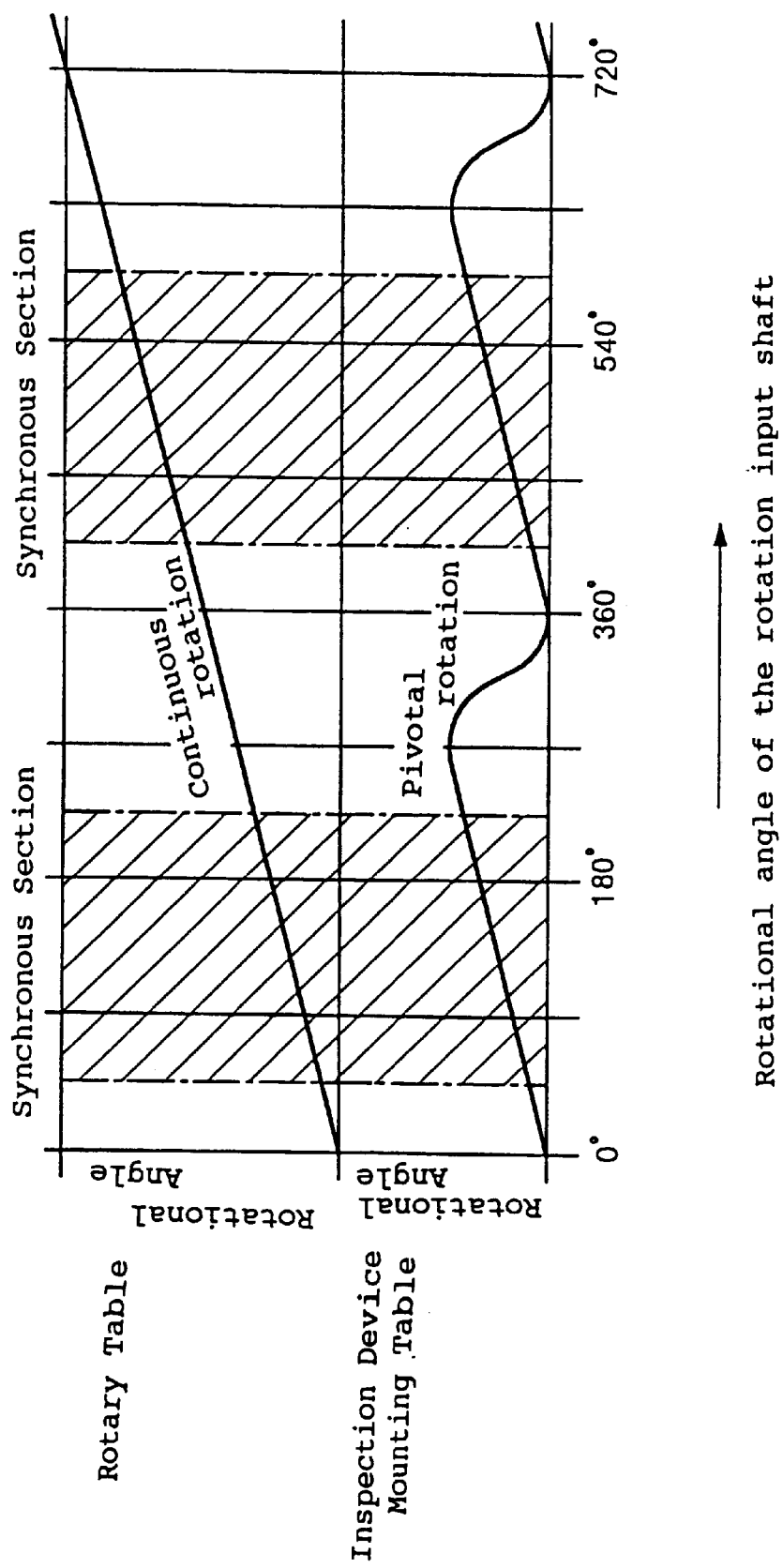
FIG. 5 is a time chart showing a motional relation between a rotary table and an inspection device mounting table both used in the inspection system.

As shown in FIG. 4, a continuous rotation output shaft 44 and a pivotal rotation output shaft 46 are disposed sideways of the continuous rotation drive cam 40 and the pivotal rotation drive cam 42. These output shafts 44 and 46 are arranged perpendicularly to the rotation input shaft 38. A circular turret 48 is fitted on the continuous rotation output shaft 44, and cam followers 50 are provided rotatably on the outer periphery of the turret 48 so as to come into sliding contact with the continuous rotation drive cam 40. On the other hand, a sectorial turret 52 is fitted on the pivotal rotation output shaft 46, and cam followers 54 are provided rotatably on the outer periphery of the turret 52 so as to come into sliding contact with the pivotal rotation drive cam 42. Therefore, with rotation of the rotation input shaft 38, the continuous rotation output shaft 44 is rotated continuously through the continuous rotation drive cam 40 and the turret 48, while the pivotal rotation output shaft 46 is pivotally rotated through the pivotal rotation drive cam 42 and the turret 52.

An output gear 56 is fixed to the upper end of the continuous rotation output shaft 44, while an input gear 58 is fixed to the lower end of the boss portion 26 of the rotary table 12. The output gear 56 and the input gear 58 are meshed with each other, whereby the rotation of the continuous rotation output shaft 44 is transmitted to the rotary table 12, so that the rotary table 12 is rotated continuously. On the other hand, the upper end of the pivotal rotation output shaft 46 is integrally connected to the lower end of the support shaft 22 of the inner table 14a, whereby the pivotal rotation of the pivotal rotation output shaft 46 is transmitted to the support shaft 22 to pivotally rotate the inspection device mounting table 14 which comprises the inner table 14a and the outer table 14b.

The inspection device mounting table 14, at its advance path, is rotated in the same direction as the rotating direction of the rotary table 12, and subsequently at its return path, is rotated in the direction opposite to the rotating direction of the rotary table 12. The cam surface of the pivotal rotation drive cam 42 which causes the inspection device mounting table 14 to reciprocate pivotally is designed such that at the advance path of the inspection device mounting table 14, the rotating speed of the table 14 is equal to that of the rotary table 12 to synchronize the rotational motions of these tables 12 and 14, while at its return path the rotating speed of the table 14 is higher than that of its advanced path to permits the table 14 to return its original position quickly. The motional relation between the rotary table 12 and the inspection device mounting table 14 is shown in terms of a time chart in FIG. 5. In the hatched areas in the same figure, both tables 12 and 14 are rendered equal to each other in the inclination of rotational angle (rotating speed) so that the tables 12 and 14 are rotated at the same speed synchronously in the same direction.

Figure 7:
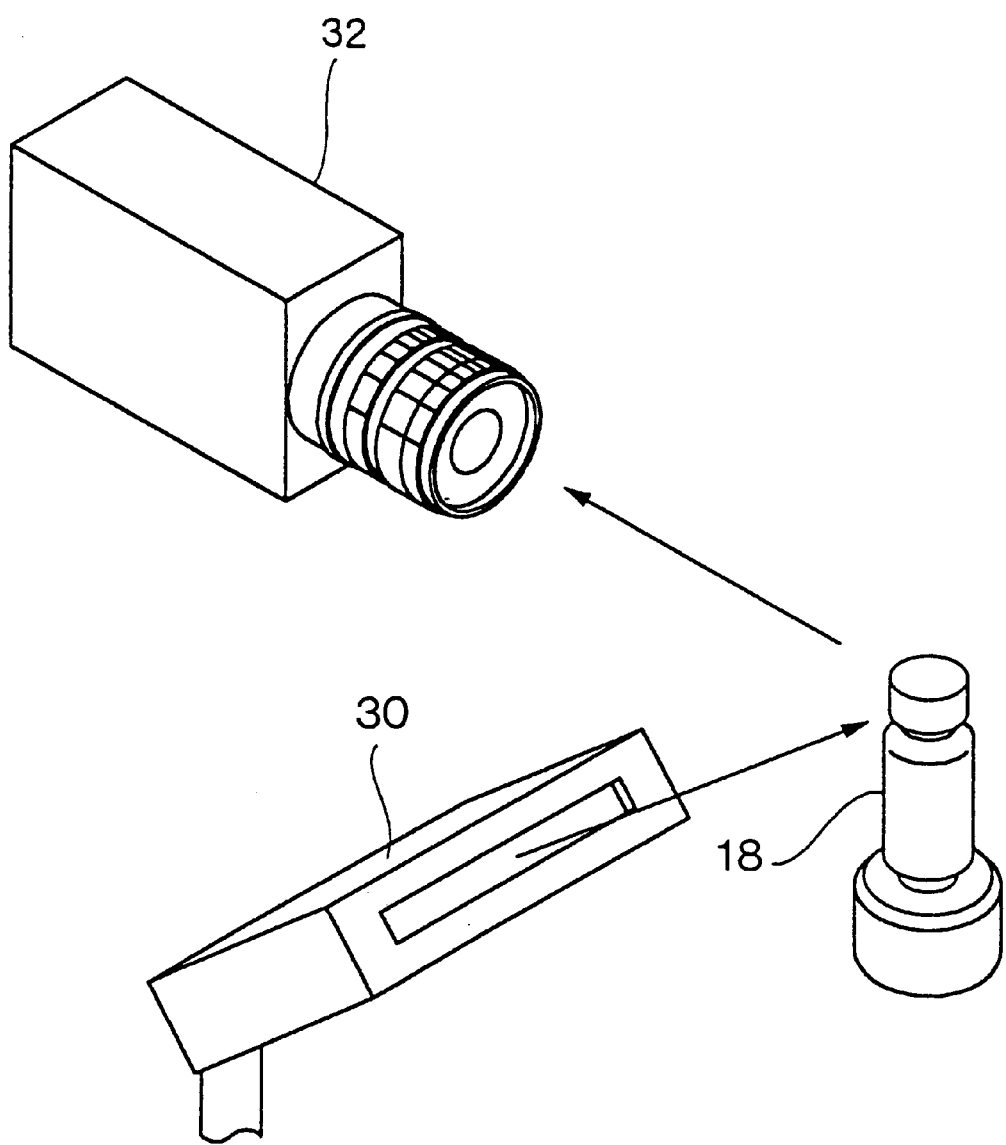
FIG. 7 is a perspective view of a principal portion showing one example of an inspection mode of a non-contact type inspection system.
Figure 8:
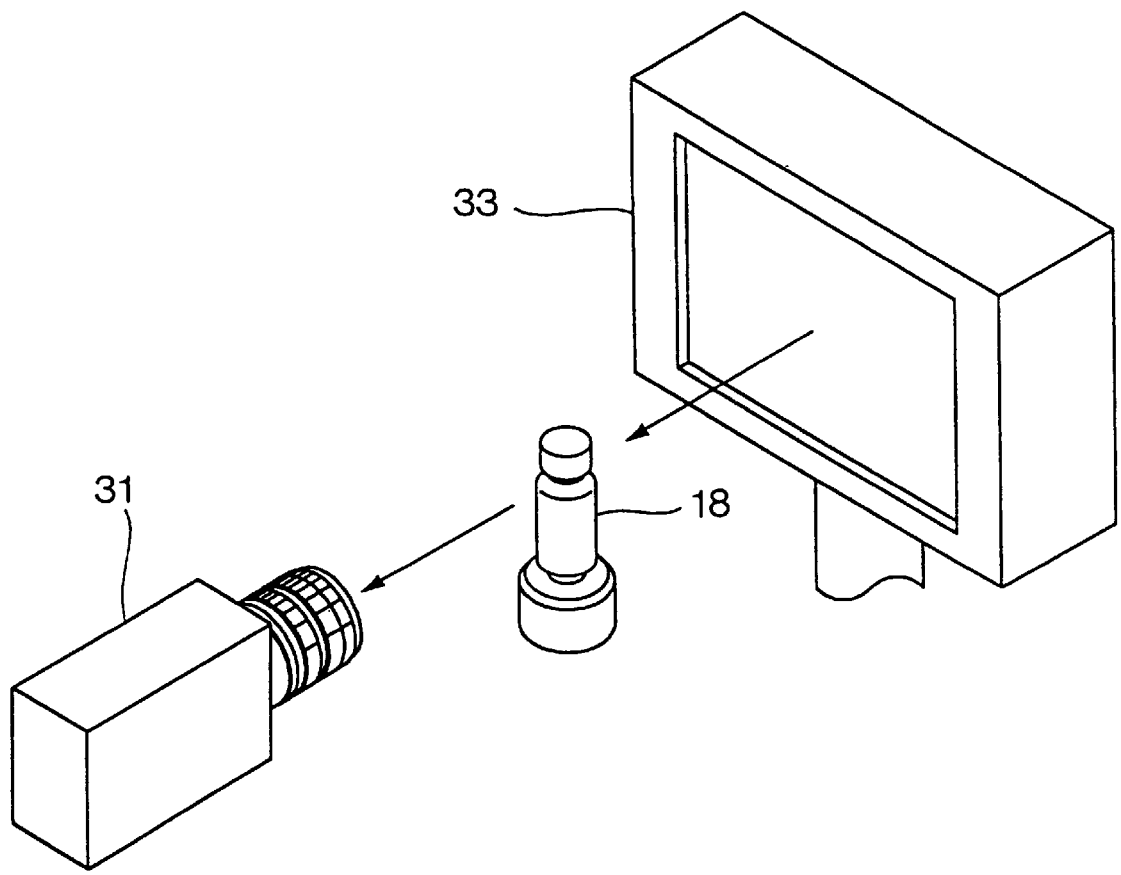
FIG. 8 is a perspective view of a principal portion showing another example of an inspection mode of the non-contact type inspection system.

To photograph the image of the products 18 to be inspected with the CCD camera 32 mounted on the inspection device mounting table 14, as shown in FIG. 7, for example, by combining the CCD camera 32 with the projector 30, the light beams irradiated by the projector 30 are reflected by the products 18 and the CCD camera 32 photographs the reflected light. In the case the products 18 are transparent vessels containing liquids such as ampoules, vials or the like, as shown in FIG. 8, by combining the transmission type sensor 31 and the backlight 33, the light beams irradiated by the backlight 33 are permitted to pass through the products 18, and the transmitted light is sensed by the transmission type sensor 31. The image photographed by the CCD camera 32 is sent to an image processor. On the other hand, the signals sensed by the transmission type sensor 31 are transmitted to a processor. And then, the appearance of the products 18 is inspected and foreign materials mixed to the contents thereof are detected if any to judge whether the products 18 are acceptable or not acceptable.

On the other hand, the feed line 16 for feeding the products 18 to be inspected onto the rotary table 12 is provided with a guide 60 for moving the products 18 in a row and in an orderly manner and a first star wheel 62 disposed at an outlet portion of the guide 60, as shown in FIG. 2. The products 18 are pushed out successively from the guide 60 and are received one by one in recesses 62a formed at equal intervals in the outer periphery of the first star wheel 62. In this state, the first star wheel 62 rotates to put the products 18 onto rotatable seats 64 successively one by one. The rotatable seats 64 are formed on the rotary table 12 to let the products 18 rotate on their own axes.

On the other hand, the discharge line 20 for discharging the products 18 to be inspected from the rotary table 12 after finishing the inspection is composed of a second star wheel 66 and a sorter 68 contiguous to the second star wheel 66. The products 18 delivered successively from the rotary table 12 are received one by one into recesses 66a which are formed at equal intervals in the outer periphery of the second star wheel 66. The second star wheel 66 rotates in this state to deliver the products 18 one by one to the sorter 68.

The sorter 68 is provided with a screw 68a for the conveyance of the products 18 which are delivered from the second star wheel 66, and a pendulum type sorting mechanism 70 for distributing the products 18 to be inspected, which are sent out one by one from the screw 68a, to a first sorting passage 70a or to a second sorting passage 70b. The pendulum type sorter 70 has a pendulum 70f. The pendulum 70f is provided so that it can reciprocate pivotally about its pivotal center O. The pendulum 70f has a pair of passages 70c and 70d bifurcately with respect to the pivotal center O. An inlet 70e is brought into communication with the first sorting passage 70a through a passage 70c or with the second sorting passage 70b through a passage 70d, alternatively in accordance a pivotal motion of the pendulum 70f centered at the pivotal center O. The products 18 conducted to the first sorting passage 70a are received in a first storage portion 72, while the products 18 conducted to the second sorting passage 70b are received in the second storage portion 72a. For example, the first storage portion 72 is used for the storage of non-defective products, while the second storage portion 72a is used for the storage of defective products.

Figure 6:
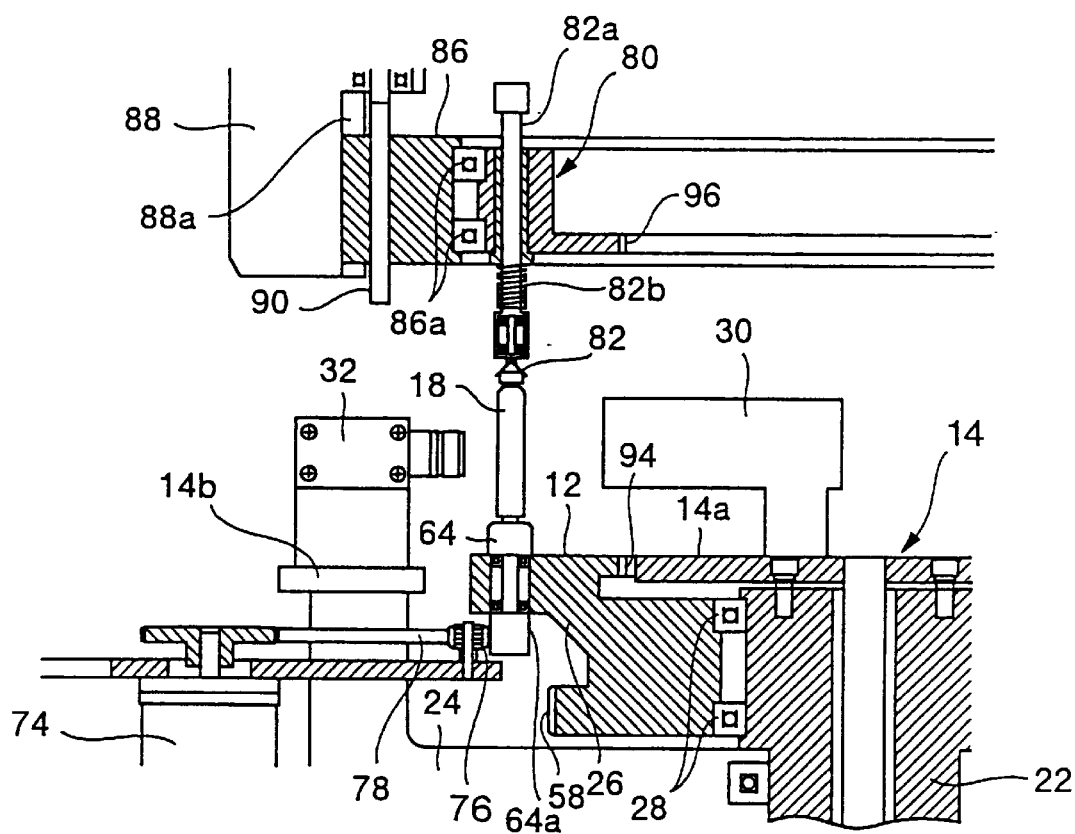
FIG. 6 is an enlarged sectional view of a principal portion of the inspection system.
Figure 9:
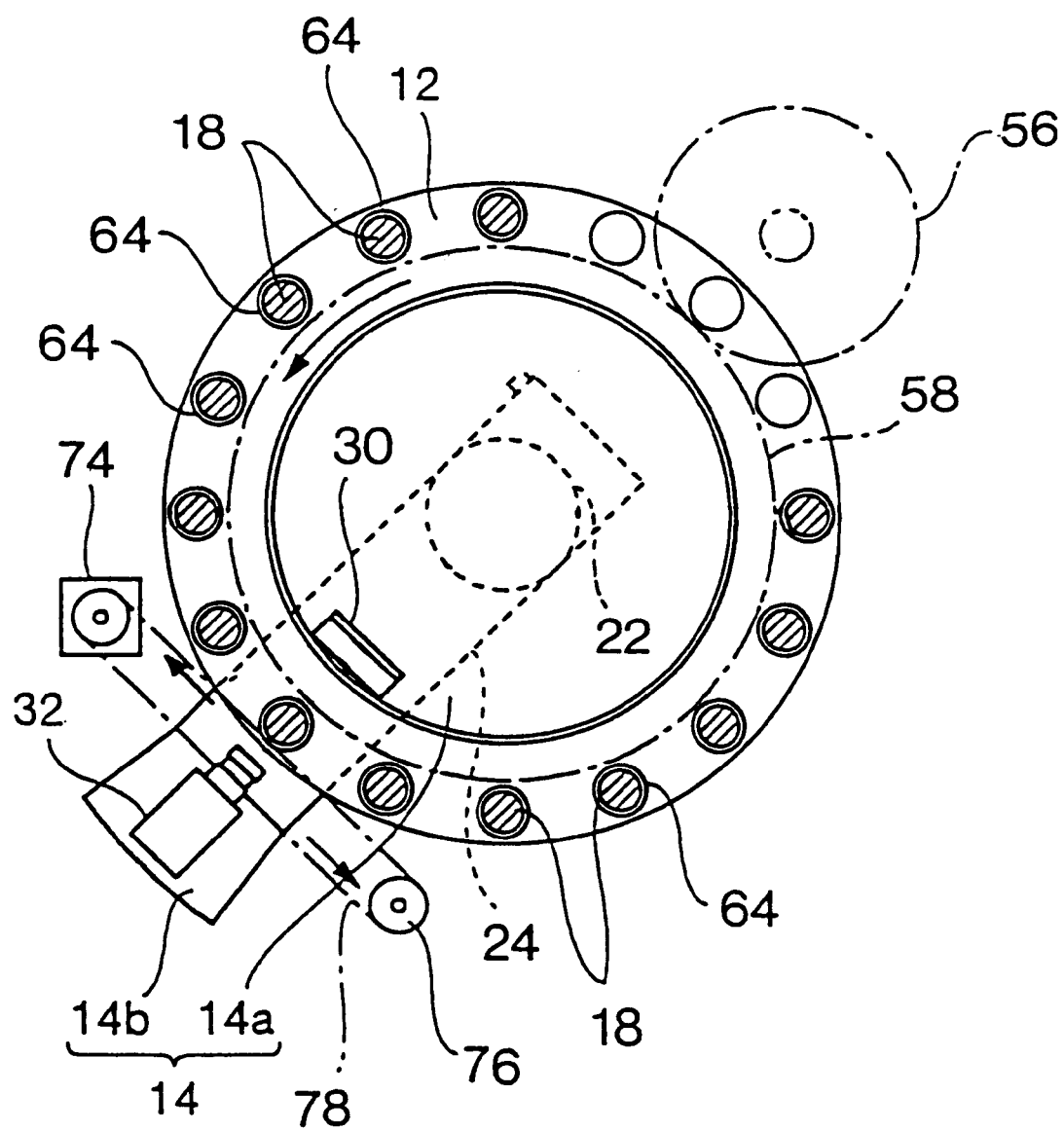
FIG. 9 is a plan view showing a mechanism which rotates the products.
Figure 10:
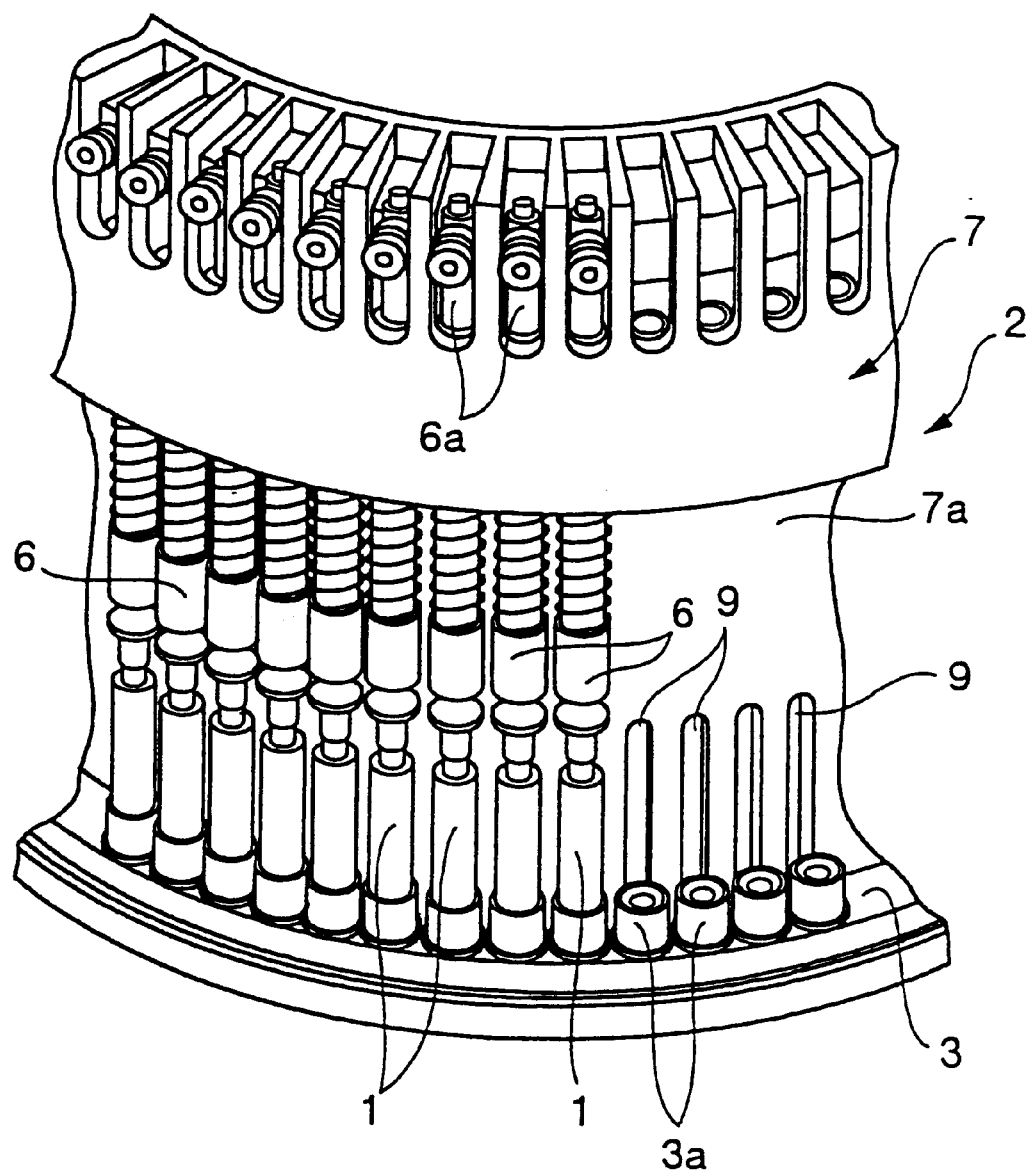
FIG. 10 is a perspective view of a principal portion of a conventional inspection system.
Figure 11:
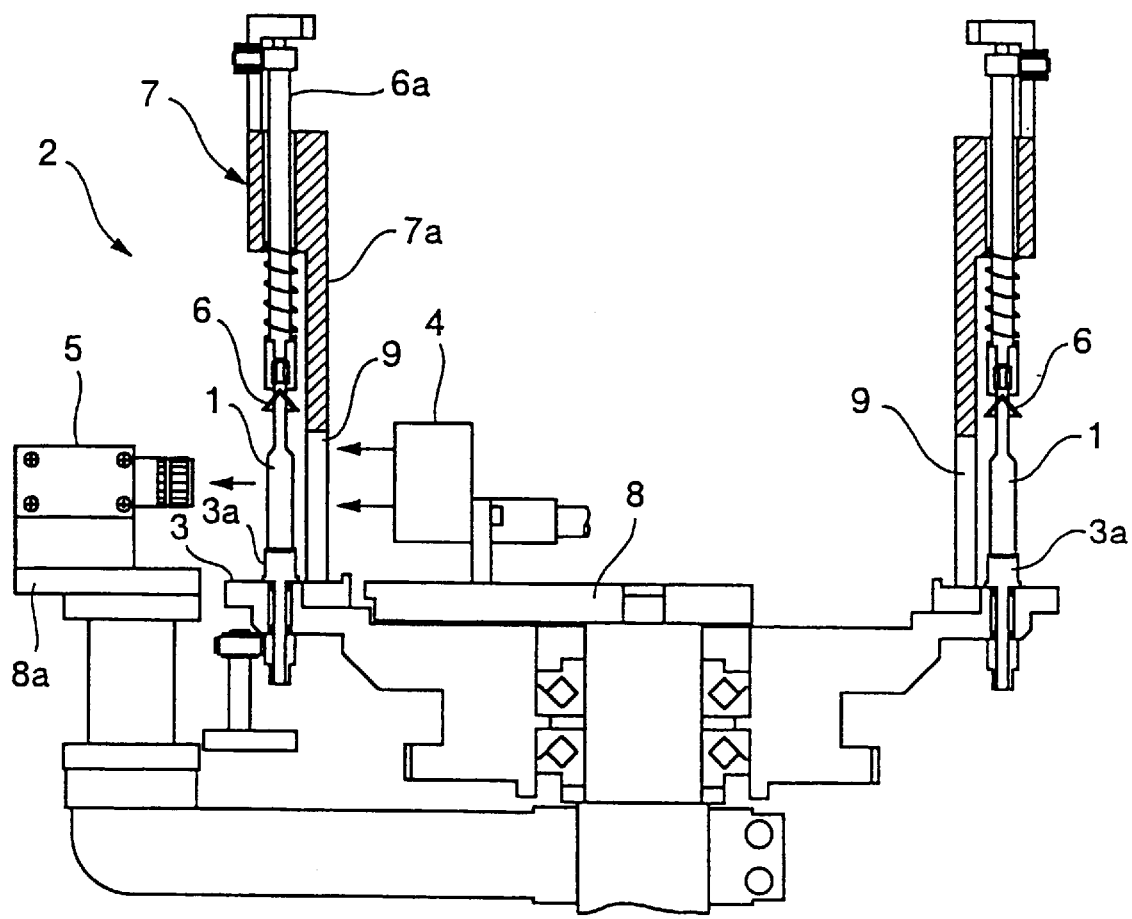
FIG. 11 is a sectional view of a principal portion of a conventional inspection system.

On the other hand, as shown in FIGS. 2, 6, and 9, spin shafts 64a suspended from the rotatable seats 64 to rotatably place the products 18 to be inspected are rotatably mounted on the rotary table 12 and are projected from the lower surface of the rotary table 12. When the product 18 reaches the position of the inspection device mounting table 14, the associated spin shaft 64a comes into sliding contact with a belt 78 which is entrained on and between a motor 74 and a pulley 76 and is driven in a circulative manner. Upon such sliding contact of the spin shaft 64a with the belt 78, the spin shaft 64a rotates and causes the rotatable seat 64 to rotate, so that the product 18 thereon is rotated on-its own axis. By such rotation of each product 18 on the rotary table 12, the whole of its outer periphery can be photographed by a single CCD camera 32 and sensing work is conducted by the transmission type sensor 31. In the case where the products 18 are, for example, ampoules or vials and the contents thereof are to be checked with transmitted light, if each product 18 which has thus been rotated on its own axis is stopped suddenly, only the contents thereof continue to rotate therein and hence it is possible to check more exactly whether a foreign matter is fixed therein or not.

The products 18 to be inspected which move with rotation of the rotary table 12 are held down at the respective upper portions by caps 82 secured to a rotary head 80. On the other hand, the non-contact type inspection system 10 is mounted to a frame 84 which surrounds the whole of the inspection system 10. In the top space of the frame 84 which space is a dead space causing no obstacle to the operation of the inspection system 10, the rotary head 80 is supported in a suspended state.

The rotary head 80 is supported above the rotary table 12 and rotatably about the rotation center of the same table 12. At the peripheral edge portion of the rotary head 80 are provided the caps 82 in corresponding relation to the rotatable seats 64 formed on the rotary table 12. As shown in FIG. 6, the caps 82 are respectively formed at the lower ends of stems 82a which are inserted into the rotary head 80 vertically slidably. The stems 82a are pressed downward through springs 82b.

The outer peripheral portion of the rotary head 80 is attached to the inner periphery of an annular lift frame 86 rotatably through bearings 86a. The lift frame 86 is mounted to the underside of the top portion of the frame 84 through a holding frame 88. The lift frame 86 is fitted vertically slidably in slide grooves 88a formed in the holding frame 88, and a plurality of bolts 90, which are rotatably fitted in the holding frame 88, are screwed into the lift frame 86. One of the bolts 90 is projected above the frame 84 and a handle 90a is provided at the upper end of the thus-projected bolt 90. Between the bolts 90 is disposed a transmission mechanism 91 comprising sprockets 91a and a chain 91b, whereby all the bolts 90 are interlocked together. With rotation of the handle 90a, the lift frame 86 moves vertically together with the rotary head 80.

Further, an interlocking mechanism 92 is disposed between the rotary table 12 and the rotary head 80 to rotate the rotary head 80 in interlock with the rotary table 12. The interlocking mechanism 92 is constituted by connecting first and second internal gears 94 and 96 with each other through first and second planetary gears 98 and 100 meshing with the first and second internal gears 94 and 96 respectively, the first and second internal gears 94 and 96 being formed in the rotary table 12 and the rotary head 80, respectively.

The first and second internal gears 94 and 96 are formed to have the same diameter. The first internal gear 94 is integrally formed in the inner periphery of the rotary table 12, while the second internal gear 96 is integrally formed in the inner periphery of the rotary head 80. The first and second planetary gears 98 and 100 are also formed at the same diameter and are positioned outside a pivotal reciprocation range of the outer table 14b which is pivotally rotated by the pivotal rotation drive cam 42 to prevent the gears 98 and 100 from interfering the motion of the table 14, as shown in FIG. 3. The first and second planetary gears 98 and 100 are integrally connected together through a connecting shaft 102, and the connecting shaft 102 is supported rotatably by a bearing member 104 fixed to the inner table 14a. The second planetary gear 100 is formed axially long, taking the amount of vertical displacement of the rotary head 80 into account.

In the non-contact type inspection system 10 of this embodiment constructed as above, when the rotation input shaft 38 is rotated to rotate both continuous rotation drive cam 40 and pivotal rotation drive cam 42, the rotary table 12 is rotated continuously by the rotation of the continuous rotation drive cam 40 via the turret 48 and the continuous rotation output shaft 44, and the inspection device mounting table 14 is pivotally rotated to and fro pivotally by the pivotal rotation drive cam 42 via the turret 52 and the pivotal rotation output shaft 46 in directions same as and opposite to the rotating direction of the rotary table 12. Then, the products 18 to be inspected are received onto the rotatable seats 64 on the rotary table 12 successively one by one from the feed line 16 and are conveyed continuously by the rotary table 12 which rotates continuously. This conveyance of the products 18 is effected stably because the upper portions of the products 18 on the rotary table 12 are held by the caps 82 of the rotary head 80.

At the advance path of the pivotally rotating, the inspection device mounting table 14 is rotated in the same direction as the rotating direction of the rotary table 12 in synchronism with the rotary table 12, so that the projector 30, the transmission type sensor 31, the CCD camera 32 and the backlight 33, which are mounted on the inspection device mounting table 14, move integrally and synchronously with the products 18 to be inspected being conveyed by the rotary table 12. During this synchronous rotation of both tables 12 and 14, the products 18 are inspected by the non-contact type inspection devices, including the CCD camera 32, whereby there can be created a state as if still products 18 were inspected by still inspection devices, and thus the inspection can be effected with a high accuracy. In the area where the rotary table 12 and the inspection device mounting table 14 move in synchronism each other, there is no relative movement among products 18, the CCD camera 32 and the transmission type sensor 31, so that if the photographing is performed continuously in this area to obtain a number of images and many sensing signals are obtained, it can be allowed to compare the plural images obtained each other and compare the sensing signals obtained each other under the same conditions and thus the high inspection accuracy is achieved. Recently, standards on the quality of chemicals, foods and drinks have been becoming more and more strict, but the inspection system of this embodiment permits a high-accuracy inspection of pin-holes of glass and fine cracks and the like. The products 18 to be inspected are not limited to those referred to above, but various other products, including electronic components, may be used as the products 18.

According to the system construction of this embodiment, even during inspection of the products 18 to be inspected, the products 18 can be conveyed by the rotary table 12 without interruption, thus ensuring a high productivity. After the inspection of the products 18 is over, the inspection device mounting table 14 is rotated promptly in the direction opposite to the rotating direction of the rotary table 12 to return its original position, and is now ready for the next inspection work.

The products 18 to be inspected having been inspected on the rotary table 12 are sent out to the discharge line 20, then non-defective products pass the screw 68a of the sorter 68 and are thereafter received into the first storage portion 72 through the passage 70c and the first sorting passage 70a by means of the illustrated pendulum 70f. On the other hand, for a defective product, the pendulum 70f is moved pivotally to store the defective product into the second storage portion 72a through the passage 70d and the second sorting passage 70b.

Although in this embodiment the light rays radiated from the projector 30 and backlight 33 are utilized to check the products 18 to be inspected, this constitutes no limitation, but such inspection devices may be substituted by inspection devices which utilize, for example, X-rays or an electromagnetic wave.

Since in this embodiment the rotary head 80 having caps 82 for holding the upper portions of the products 18 to be inspected is supported above the rotary table 12 in a suspended state from the top portion of the frame 84 through both holding frame 88 and lift frame 86, an open space including no obstacle can be formed throughout the whole circumference of both rotary table 12 and rotary head 80 above the rotary table 12 and below the rotary head 80. Thus, when the products 18 are inspected by such non-contact type inspection devices as the projector 30, the transmission type sensor 31, the CCD camera 32 and the backlight 33, there is no obstruction between those inspection devices arranged in a sandwiching relation to the rotary table 12 and the products 18 carried on the rotary table 12. Consequently, the inspection ability of the inspection devices can be exhibited to a satisfactory extent, the layout of the inspection devices for the products 18 can be set freely, and the inspection of the products 18 by the inspection devices can be conducted with a high accuracy and over a wide range.

The lift frame 86, which holds the rotary head 80 rotatably, is mounted to the holding frame 88 fixed to the frame 84, in a vertically movable manner through bolts 90. Thus, the rotary head 80 is moved vertically by operation of the handle 90a. By moving the rotary head 80 up and down to adjust its height, it becomes possible to inspect plural products 18 of different heights using a single inspection system.

Further, the rotary head 80, which is supported in a suspended state from the top of the frame 84, is interlocked with the rotary table 12 by means of the interlocking mechanism 92. The interlocking mechanism 92 is composed of first and second internal gears 94 and 96 formed in the rotary table 12 and the rotary head 80, respectively, and a pair of first and second interconnected planetary gears 98 and 100 meshing with the first and second internal gears 94 and 96, respectively. The first and second planetary gears 98 and 100 are supported by the inspection device mounting table 14. With this construction, when the first internal gear 94 is rotated together with the rotary table 12, the first planetary gear 98 meshing with the first internal gear 94 and the second planetary gear 100 connected to the first planetary gear 98 through the connecting shaft 102 rotate, and further the second internal gear 96 meshing with the second planetary gear 100 also rotates, whereby the rotary head 80 can be rotated in synchronism with the rotary table 12.

Since the first and second planetary gears 98 and 100 are supported by the inspection device mounting table 14 through the bearing member 104, even if the table 14 relatively rotates with respect to the rotary table 12, the first and second internal gears 94 and 96 can be rotated at an equal speed and hence both rotary table 12 and rotary head 80 can be rotated synchronously at all times. In particular, during the period of inspection at which the rotary table 12 and the inspection device mounting table 14 rotate synchronously, there occurs no relative rotation between the tables 12 and 14, so the first and second planetary gears 98 and 100 do not rotate. Thus, although the interlocking mechanism 92 is used, it does not occur any vibration caused by the application of the interlocking mechanism 92. That is, the inspection can be carried out in a vibration-free state and an extremely high accuracy of inspection work can be ensured.

Further, to drive the rotary table 12 and the inspection device mounting table 14 in the present embodiment, by using the continuous rotation drive cam 40 and the pivotal rotation drive cam 42, the rotation of the rotation input shaft 38 is converted into the continuous rotation of the rotary table 12 and the pivotal rotation of the inspection device mounting table 14. Thus there is no backlash in motion transfer and can be always realized the accurate operation. Further, by providing the rotary table 12 with the positioning grooves and holes or the like for the products 18 to be inspected on the surface thereof, the positioning accuracy of the products 18 is enhanced and it is possible to eliminate the blur of image and falling out of focus. Further, it can be allowed to mount the CCD camera 32 and the transmission type sensor 31 on the inspection device mounting table 14 in the direction desired to be inspected, which makes it possible to perform a number of items of inspections at one time.

As set forth above, according to the non-contact type inspection system in the first aspect of the present invention, since the rotary head which holds the upper portions of test samples to be inspected is supported above the rotary table, an open space free of any obstacle can be formed throughout the whole circumference of both rotary table and rotary head above the rotary table and below the rotary head. Thus, in inspecting the test samples by the non-contact type inspection devices, there is no obstruction between the inspection devices and the test samples. Accordingly, the inspection ability of the inspection devices can be exhibited to a satisfactory extent, the layout of the inspection devices for test samples can be designed freely, and thus the inspection of test samples by the inspection devices can be performed with a high accuracy and over a wide range.

Moreover, since the rotary head is supported in the space above the rotary table which space is a dead space located above the test sample conveying path and including no obstacle in the system construction, it is not necessary to ensure any special space for mounting of the rotary head. An appropriate layout of the rotary head can be realized by effectively utilizing such dead space.

According to the non-contact type inspection system in the second aspect of the present invention, since the rotary head is supported vertically movably, the test sample holding position by the rotary head can be varied up and down, whereby plural test samples of different heights can be inspected using a single inspection system.

Further, according to the non-contact type inspection system in the third aspect of the present invention, the interlocking mechanism comprises a pair of first and second internal gears formed in the rotary table and the rotary head, respectively, a pair of first and second planetary gears meshing with the first and second internal gears, respectively, and a connecting shaft supported by the inspection device mounting table to connect the first and second planetary gears integrally with each other. Accordingly, when the first internal gear is rotated together with the rotary table, the first planetary gear meshing with the first internal gear and the second planetary gear connected to the first planetary gear rotate, and the second internal gear meshing with the second planetary gear also rotates. In this way the rotary head can be rotated in synchronism with the rotary table.

In particular, since the first and second planetary gears are supported by the inspection device mounting table, the first and second internal gears can be rotated at an equal speed, and the rotary table and the rotary head can be rotated synchronously at all times, irrespective of whether the inspection device mounting table is a fixed type or a rotatable type which is relatively rotated as necessary with respect to the rotary table.

Furthermore, according to the present invention, the rotation input shaft is rotated to rotate the continuous rotation drive cam and the pivotal rotation drive cam, the rotary table is rotated continuously via the turret and the continuous rotation output shaft, and similarly the inspection device mounting table is rotated continuously to rotate pivotally via the turret and the pivotal rotation output shaft. Thereby, test samples is conveyed continuously by the rotary table being rotating continuously. Meanwhile, since the inspection device mounting table is rotated in synchronism with the rotary table when it is rotated in the same direction as the rotating direction of the rotary table, the non-contact type inspection device mounted on the inspection device mounting table is moved together in synchronism with the test samples conveyed by the rotary table. During the synchronous rotation of both tables, the test samples can be inspected by the non-contact type inspection device, whereby there can be realized the state as if the still test samples are inspected by the still inspection device, so that the inspection can be effected with high accuracy.

Further, since when the inspection for test samples is carried out by the non-contact type inspection device, the test samples can be conveyed by the rotary table without interruption, thus ensuring a high productivity.

Still further, in the present invention, the continuous rotation of the rotary table and the pivotal rotation of the inspection device mounting table can be obtained by the use of the continuous rotation drive cam and the pivotal rotation drive cam. Accordingly, there is no backlash in a series of motion transfer, accurate operation can be realized continuously and the accurate rotational motion of the tables can be realized. Thus, the present invention exhibits the effects of enhancing the inspection accuracy in the inspection work liable to be effected by the accuracy of the rotational motion of the tables.

What is claimed is:

1. A non-contact type inspection system comprising:
    an annular rotary table which is rotated to convey test samples;
    an inspection device mounting table disposed inside and outside said rotary table in a sandwiching relation to said rotary table, said inspection device mounting table being pivotally rotatable with the rotation of said rotary table around a rotation center of said rotary table, and having a non-contact type inspection device mounted on said inspection device mounting table for inspection of said test samples passing through said inspection system by conveyance on said rotary table;
    a rotary head which is supported above said rotary table and rotatably about the rotation center of said rotary table to hold the upper portions of said test samples being conveyed by said rotary table;
    an interlocking mechanism for rotating said rotary head in synchronism with said rotary table;
    a rotation input shaft which is driven rotatively, and having a continuous rotation drive cam and a pivotal rotation drive cam being coaxially mounted on said rotation input shaft side by side;
    a continuous rotation output shaft which is rotated continuously through a first turret, said first turret being in sliding contact with said continuous rotation drive cam; and
    a private rotation output shaft which is rotated pivotal through a second turret, said second turret being in sliding contact with said pivotal rotation drive cam;
    wherein said rotary table is rotated continuously by said continuous rotation output shaft, said inspection device mounting table is pivotally rotated by said pivotal rotation output shaft, and when said inspection device mounting table is rotated in the same direction as the rotating direction of said rotary table, said inspection device mounting table is rotated in synchronism with said rotary table.

2. A non-contact type inspection system according to claim 1, wherein said rotary head is supported vertically movably.

3. A non-contact type inspection system according to claim 1, wherein said interlocking mechanism includes a planetary gear mechanism which comprises:
    a pair of first and second internal gears formed in said rotary table and said rotary head, respectively;
    a pair of first and second planetary gears meshing with said first and second internal gears, respectively; and
    a connecting shaft supported by said inspection device mounting table to connect said first and second planetary gears integrally with each other.

4. A non-contact type inspection system according to claim 3, wherein said first and second internal gears have the same module and are integrally formed on the inner periphery of said rotary table and the inner periphery of said rotary head, respectively, said first and second planetary gears also have the same module, and said connecting shaft for connection of both said planetary gears is supported rotatably by a bearing member provided on said inspection device mounting table.

5. A non-contact type inspection system according to claim 3, wherein said rotary head is supported vertically movably and said second planetary gear meshing with said second internal gear in said rotary head is formed axially long in proportion to the vertical displacement of said rotary head.

6. A non-contact type inspection system according to claim 2, further including:
    a holding frame disposed above said rotary table and formed with a vertically extending slide groove;
    an annular lift frame mounted to said holding frame vertically movably through said slide groove; and
    a bearing provided on the inner periphery of said lift frame to support the outer periphery of said rotary head rotatably,
    wherein said rotary head being suspended from said holding frame vertically movably and rotatably through said lift frame.

7. A non-contact type inspection system according to claim 6, further including:
   said lift frame which is mounted to said holding frame vertically movably through said slide groove;
   bolts supported rotatably by said holding frame and screwed to be engaged with said lift frame; and
   a power transfer mechanism comprising sprockets mounted on said bolts and a chain entrained on said sprockets for the transfer of a driving force.

8. A non-contact type inspection system according to claim 1, wherein said rotary table is provided with an input gear, an output gear is provided on said continuous rotation output shaft and is in mesh with said input gear, said turret associated with said continuous rotation output shaft is circular and is mounted on said continuous rotation output shaft, and cam followers are provided rotatably on the outer periphery of said circular turret so as to come into sliding contact with said continuous rotation drive cam.

9. A non-contact type inspection system according to claim 1, wherein a support shaft is provided at a rotation center position of said inspection device mounting table, said pivotal rotation output shaft is connected to said support shaft, said turret associated with said pivotal rotation output shaft is sectorial and is mounted on said pivotal rotation output shaft, and cam followers are provided rotatably on the outer periphery of said sectorial turret so as to come into sliding contact with said pivotal rotation drive cam.

10. A non-contact type inspection system according to claim 1, wherein said continuous rotation drive cam and said pivotal rotation drive cam, which determine the rotating speed of said rotary table and that of said inspection device mounting table, have cam curves designed such that at a timing at which said inspection device mounting table rotates in the same direction as the rotating direction of said rotary table, the rotating speed of said inspection device mounting table and that of said rotary table are equal to each other, while at a timing at which said inspection device mounting table rotates in the direction opposite to the rotating direction of said rotary table, the rotating speed of said inspection device mounting table is higher than that of said rotary table.

11. A non-contact type inspection system according to. claim 1, wherein said rotary table is formed in an annular shape, said inspection device mounting table comprises an inner table disposed in a space inside said rotary table and an outer table disposed in a space outside said rotary table in an opposed relation to said inner table, a support shaft is integrally provided at a-rotation center position of said inner table, an arm extending to the outside of said rotary table is integrally provided on said support shaft, and said outer table is integrally mounted to said arm.

12. A non-contact type inspection system according to claim 11, wherein said non-contact type inspection device is disposed on each of said inner table and said outer table in an opposed relation with said rotary table and said test samples being conveyed are located therebetween.

13. A non-contact type inspection system according to claim 12, wherein said non-contact type inspection device comprises a projector for radiating light to be reflected by each of said test samples and a CCD camera for photographing each of said test samples to obtain an image thereof, said projector and said CCD camera being disposed on said inner table and said outer table, respectively, an image of the reflection reflected by each said test sample by the light radiated from said projector is photographed by said CCD camera and said test sample is inspected on the basis of the image thereof thus obtained.

14. A non-contact type inspection system according to claim 12, wherein said non-contact type inspection device comprises a backlight for radiating light to pass through each of said test samples and a transmission type sensor for sensing the thus-transmitted light, said backlight and said transmission type sensor being disposed on said inner table and said outer table, respectively, and the transmitted light through each said test sample after radiation from said backlight is sensed by said transmission type sensor to inspect said test sample.

15. A non-contact type inspection system according to claim 1, wherein said non-contact type inspection device utilizes X-rays and an electromagnetic wave.

16. A non-contact type inspection system according to claim 1, wherein said rotary head is provided with stems inserted therein vertically slidably and springs for urging said stems downward, and caps for holding the upper portions of said test samples are provided respectively at the lower ends of said stems.

17. A non-contact type inspection system according to claim 1, wherein a feed line for feeding said test samples onto said rotary table and a discharge line for discharging said samples from said rotary table are disposed around said rotary table spaced apart from each other in the circumferential direction of said rotary table.

* * * * *